United States Patent
Araki et al.

[11] 4,014,211
[45] Mar. 29, 1977

[54] ULTRASONIC FLOW METER

[75] Inventors: Hitoshi Araki; Yoshihioro Matsunaga, both of Amagasaki, Japan

[73] Assignee: Mitsubishi Denki Kabushiki Kaisha, Tokyo, Japan

[22] Filed: Oct. 21, 1975

[21] Appl. No.: 624,576

[52] U.S. Cl. .......................... 73/194 A; 73/71.5 US
[51] Int. Cl.² .......................................... G01F 1/66
[58] Field of Search ......... 73/194 A, 67.5, 71.5 US

[56] References Cited
UNITED STATES PATENTS

| | | | |
|---|---|---|---|
| 2,669,121 | 2/1954 | Garman et al. | 73/194 A |
| 2,697,936 | 12/1954 | Farrow | 74/67.9 |
| 3,320,797 | 5/1967 | Tajiri et al. | 73/71.5 US X |
| 3,575,050 | 4/1971 | Lynnworth | 73/194 A |
| 3,738,169 | 6/1973 | Courty | 73/194 A |

*Primary Examiner*—Charles A. Ruehl
*Attorney, Agent, or Firm*—Wenderoth, Lind & Ponack

[57] ABSTRACT

In an ultrasonic flow meter for measuring the flow rate of a fluid flowing through a pipe by determining the frequency difference between ultrasonic waves traveling within the fluid in the direction of flow of the fluid and in a direction opposite thereto, respectively. Each of the ultrasonic transmitters and receivers is connected to the pipe through an individual guide rod having disposed on its outer surface ridges which are adapted to cause ultrasonic waves reflected from the ridged surface to conceal one another out, and a thin gold sheet interposed between the guide rod and the pipe.

4 Claims, 8 Drawing Figures

ULTRASONIC FLOW METER

BACKGROUND OF THE INVENTION

This invention relates to an ultrasonic flow meter device for measuring the flow rate of a high temperature fluid flowing through a pipe.

Conventional ultrasonic flow meters have generally included one connector connecting each of several ultrasonic transmitters and receivers to the particular pipe through which a fluid to be measured flows, and oil or grease fills gaps formed on the interfaces between the connector and the mating transmitter or receiver and between the connector and the outer wall surface of the pipe. The purpose of the oil or grease is to increase the transmissibility of the ultrasonic waves on these interfaces. With the measured fluid maintained at a temperature as high as about 500° C, such as molten alkali metals, the oil or grease filling the gaps as above described can not remain intact. Thus such ultrasonic flow meters have not been capable to measuring the flow rate of high temperature fluid.

SUMMARY OF THE INVENTION

Accordingly, it is an object of the present invention to provide a new and improved ultrasonic flow meter device capable of measuring the flow rate of high temperature fluids.

The present invention accomplishes this object by the provision of an ultrasonic flow meter device comprising a pipe through which a fluid to be measured flows, first ultrasonic transmitter and receiver means disposed on the outer wall surface of the pipe and including a propagation path for an ultrasonic wave running within the fluid in the direction of flow thereof to produce a first sing-around frequency, second ultrasonic transmitter and receiver means disposed on the outer wall surface of the pipe and including a propagation path for an ultrasonic wave running within the fluid in a direction opposite to the direction of flow of the fluid to produce a second sing-around signal, and detector means for detecting the difference between the first and second sing-around frequencies to measure the flow rate of the fluid, wherein each of the first and second ultrasonic transmitter and receiver means has an ultrasonic transmitter element and an ultrasonic receiver element each fixedly secured to the outer wall surface of the pipe through a guide rod having on the outer peripheral surface thereof a plurality of ridges so that ultrasonic waves reflected from the ridged surface cancel one another out.

Preferably the guide rod may have one end surface abutting against the outer wall surface of the pipe through a thin sheet formed of a metallic material selected from the group consisting of gold, platinum, gold alloys and platinum alloys.

Advantageously a flange member may be connected to the guide rod and fastened to the outer wall surface of the pipe through bolt means or screw means thereby to fixedly secure the guide rod to the pipe through the thin metallic sheet.

BRIEF DESCRIPTION OF THE DRAWINGS

The present invention will become more readily apparent from the following detailed description taken in conjunction with the accompanying drawings in which.

DESCRIPTION OF THE PREFERRED EMBODIMENTS

Figure 1:
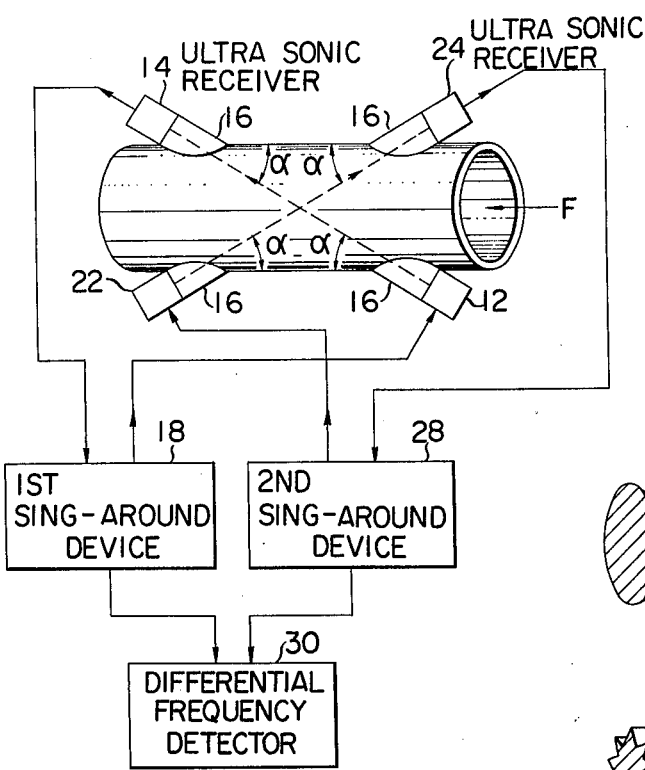
FIG. 1 is a block diagram of a conventional ultrasonic flow meter useful in explaining the principles thereof with parts illustrated in perspective.

Referring now to FIG. 1 of the drawings, there is illustrated an ultrasonic flow meter constructed in accordance with the principles of the prior art. The arrangement illustrated comprises a pipe 10 having a fluid to be measured flowing therethrough in the direction of the arrow F, a first ultrasonic transmitter element 12 and a first ultrasonic receiver element 14 fixedly secured to the outer wall surface of the pipe 10 through respective wedge-shaped connectors 16 so as to be opposite to each other and be at a predetermined angle of $\alpha$ to a line parallel to the longitudinal axis of the pipe 10. The arrangement further comprises a second ultrasonic transmitter element 22 and a second ultrasonic receiver element 24 fixedly secured to the outer wall surface of the pipe 10 through respective wedge-shaped connectors 16 in the same manner as the first transmitter and receiver elements 12 and 14 respectively. All the elements, 12, 14, 22 and 24 are disposed in a substantially common plane passing through the longitudinal axis of the pipe 10 while the first and second transmitter elements 12 and 22 are substantially aligned with the second and first receiver elements 24 and 14 in a direction perpendicular to the longitudinal axis of the pipe 10 respectively.

In the arrangement of FIG. 1, an ultrasonic wave delivered from the first ultrasonic transmitter element 12 passes through the mating connector 16 and the adjacent portion of the outer wall of the pipe 10 to the stream of fluid F within the pipe 10. Then it traverses the stream of fluid F at the predetermined angle of $\alpha$ in the direction of flow of the fluid until it reaches that portion of the outer wall of the pipe 10 to which the connector 16 for the receiver element 14 is connected. Thereafter the ultrasonic wave is received by the receiver element 14 through the mating connector 16.

An ultrasonic wave from the second ultrasonic transmitter element 22 is similarly received by the second ultrasonic receiver element 24 but it is noted that the second ultrasonic wave traverses the stream of fluid F at the predetermined angle of $\alpha$ in a direction opposite to the direction of flow of the fluid.

As shown in FIG. 1, the first ultrasonic transmetter and receiver elements 12 and 14 respectively are connected to a first sing-around device 18 to form a first transmitter and receiver system. Similarly the second ultrasonic transmitter and receiver elements 22 and 24 respectively are connected to a second sing-around device 28 to form a second transmitter and receiver system. The sing-around device 18 or 28 is operative to drive the associated transmitter element 12 or 22 to deliver the ultrasonic wave and to convert the ultrasonic wave received by the associated receiver element to a corresponding electrical signal in a manner well known in the art.

Both sing-around devices 18 and 28 are connected to a differential frequency meter 30 for comparing sing-around frequencies from the devices 18 and 28 to detect a difference therebetween.

The sing-around frequencies from the first and second transmitter and receiver systems vary in accordance with a speed at which the fluid F to be measured flows through the pipe 10. The higher the flow speed of the fluid F the shorter the time interval required for the ultrasonic wave from the first transmitter element 12 to be propagated to the first receiver element 14 of the first transmitter and receiver system and therefore the higher the first sing-around frequency which is the reciprocal of the required time interval as above described. On the contrary, if the fluid F has a reduced flow speed then the sing-around frequency of the second transmitter and receiver system will become less.

The sing-around frequencies from the first and second transmitter and receiver systems are applied to the differential frequency meter 30 where a difference between the two frequencies is detected to provide a measure of the flow speed of the fluid F. Therefore by maintaining the cross sectional area of the pipe 10 constant, the flow rate of the fluid F can be measured without any opening or the like being in the outer wall of the pipe.

In conventional flow meters such as shown in FIG. 1, it has been essential to fill gaps which may occur at the interfaces between the first transmitter, second transmitter, the first receiver and the second receiver and the connectors and between the connectors and the outer wall surface of the pipe with an oil or a grease in order to increase the transmissibility of an ultrasonic wave at those interfaces. However, if the fluid to be measured is for example, a molten alkali metal at about 500° C, the oil or grease filling the gaps as above described will not remain intact because the fluid is at a high temperature. For this reason, the ultrasonic type of flow meters such as shown in FIG. 1 can not be used for the measurement of fluids at high temperatures.

The present invention seeks to eliminate the objection to the prior art device as above described by the provision of an ultrasonic flow meter capable of measuring the flow rate of fluids at high temperatures.

Figure 2:
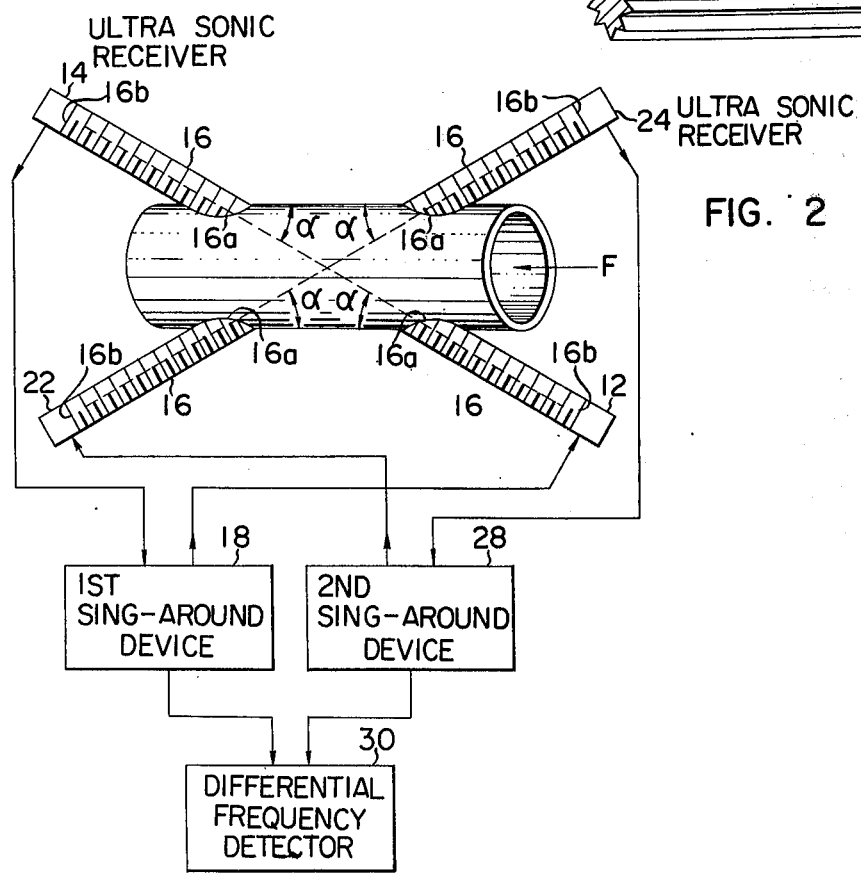
FIG. 2 is a block diagram of an ultrasonic flow meter embodying the principles of the present invention with parts illustrated in perspective.

Referring now to FIG. 2, wherein like reference numerals designate the components identical to or corresponding to those shown in FIG. 1, there is illustrated an ultrasonic flow meter constructed in accordance with the principles of the present invention. The arrangement illustrated is different from that shown in FIG. 1 principally in the construction of the connector for connecting each of the ultrasonic transmitter and receiver elements to the outer wall surface of the pipe. Each of the connectors 16 serving to propagate an ultrasonic wave therealong is in the form of a guide rod and includes one end surface formed into an abutting surface 16a causing the guide rod to be fixedly secured to a predetermined portion of the outer wall surface of the pipe 10 so as to form a predetermined angle $\alpha$ between the longitudinal axes of the rod and pipe. Each connector or guide rod 16 has the other end surface formed into a mounting surface 16b for one of the ultrasonic transmitter and receiver elements 12, 14, 22 or 24 respectively. However, means for fixedly securing the guide rod 16 to the pipe 10 as above described and means for mounting the transmitter and receiver elements to the guide rod are not illustrated in FIG. 2 for purposes of keeping the figure simple.

Figure 3:
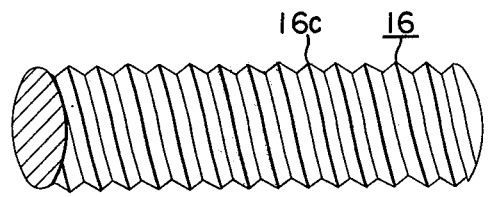
FIG. 3 is a fragmental perspective view of the ultrasonic guide rod shown in FIG. 2.
Figure 4:
FIG. 4 is a view similar to FIG. 3 but illustrating a modification of the guide rod shown in FIG. 3.

According to the principles of the present invention, the guide rod 16 is provided on outer peripheral surface thereof with a plurality of ridges in a predetermined regular pattern so that during the propagation of an ultrasonic wave along the guide rod from one to the other end, those portions of the ultrasonic wave reflected from the ridged surface thereof are damped and disappear. For example, FIG. 3 shows a guide rod 16 provided on the outer peripheral surface thereof with spiral ridges or threads 16a having a predetermined pitch while FIG. 4 shows a guide rod 16 having a plurality of longitudinal ridges 16c disposed at predetermined equal angular intervals on the entire outer peripheral surface thereof. If desired, the ridges on the guide rod 16 may have any desired configuration other than those shown in FIGS. 3 and 4.

Assuming that a fluid F flowing through the pipe 10 is even on the order of 500° C, the first and second ultrasonic transmitters 12 and 22 as well as the first and second ultrasonic receiver elements 14 and 24 as shown in FIG. 2 can be mounted on respective mounting surfaces 16b maintained at low temperatures because all the elements are connected to the pipe 10 through the individual guide rods 16. As a result, conventional mounting means can be used to mount the transmitter and receiver elements on the mounting surfaces 16b of the mating guide rods 16.

On the other hand, each of the guide rods 16 has the abutting surface 16a maintained at a high temperature. This leads to the necessity of using connection means capable of withstanding such a high temperature and having excellent transmissibility of ultrasonic waves. Further, in the measuring device embodying the principles of the present invention it is essential to increase the accuracy of the distance between each of the first and second ultrasonic transmitter elements 12 or 22 and the associated ultrasonic receiver elements 14 or 24. In addition, measuring devices with which the present invention is concerned are, in may cases, assembled in the field. Thus it is necessary to provide mounting means for easily assembling the devices in the field with a predetermined accuracy and without the necessity of performing special operations.

Figure 5:
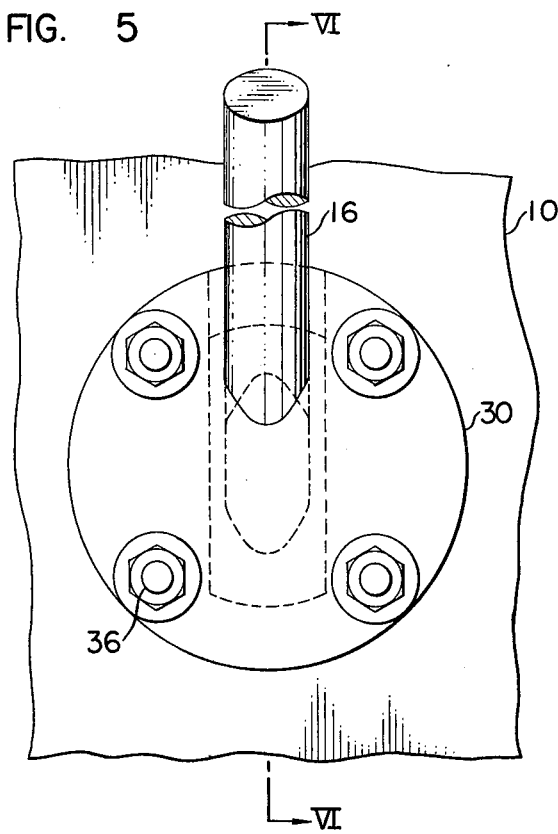
FIG. 5 is a fragmental plan view of a mounting for an ultrasonic guide rod constructed in accordance with the principles of the present invention.
Figure 6:
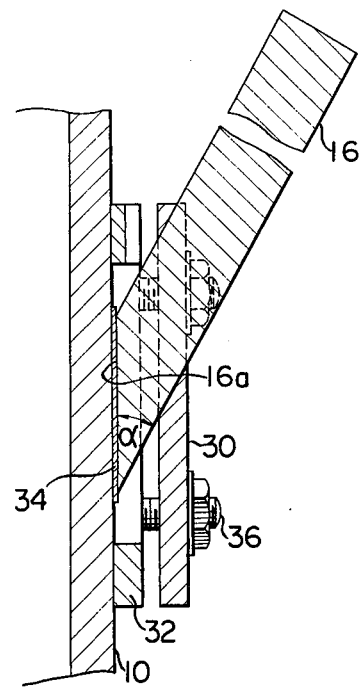
FIG. 6 is a longitudinal sectional view taken along the line VI—VI of FIG. 5.

FIG. 5 shows a plan view of mounting means for the guide rod constructed in accordance with the principles of the present invention to meet the requirements as above described and FIG. 6 shows a longitudinal sectional view of the mounting means shown in FIG. 5 with the section being taken along the line VI—VI of FIG. 5. As best shown in FIG. 6, the guide rod 16 includes the abutting surface 16a formed to abut against the outer wall surface of the pipe 10 at the predetermined angle of $\alpha$ thereto and a disc-shaped flange 30 fixed thereto as by welding so as to be substantially parallel to the abutting surface 16a of the guide rod 16. Then a disc-shaped mounting seat 32 substantially equal in outside diameter to the flange 30 is fixedly secured to the outer wall surface of the pipe 10 at such a predetermined position that an elongated opening disposed along the diameter of the seat permits the abutting surface 16a of the guide rod 16 to abut against a predetermined portion of the outer wall pipe surface through a filler 34 in the form of a thin sheet interposed therebetween and within the opening. A plurality, in this case four, of bolts 36 on the mounting seat 32 extend through the flange 30 and have nuts theaded thereon to press and fix the abutting 16a of the guide rod 16 against and to the predetermined portion of the outer wall surface of the pipe 10 by the engagement of flange 30 with guide rod 16.

The filler 34 is preferably a thin gold sheet and subject to a plastic deformation, by means of the action of the force exerted by the nuts on the bolts 36 acting on flange 30, to fill any gap between the abutting surface 16a of the guide rod 16 and the adjacent portion of the outer wall surface of the pipe 10. This results in an increase in transmissibility of the ultrasonic waves at the interface therebetween.

In the mounting means as shown in FIGS. 5 and 6, the filler 34 is required to have suitable plasticity and heat resistance at the operating temperature involved. In other words, the filler 34 is required to have a high melting point, oxidation resistance etc. Suitable examples of the material of the filler 34 are, in addition to gold, platinum, gold alloys, platinum alloys etc. In this connection, it has been found that copper, aluminum etc. have inferior oxidation resistance as compared to the material of the filler 34 as above specified and decrease the transmissibility of the ultrasonic waves.

It has been found also that the guide rod 16 should preferably formed of Hastelloy (trade mark), SUS27(-JIS) which corresponds to SISI364(ASTM) or the like from the standpoint of the transmissibility of ultrasonic waves, the workability etc.

Figure 7:
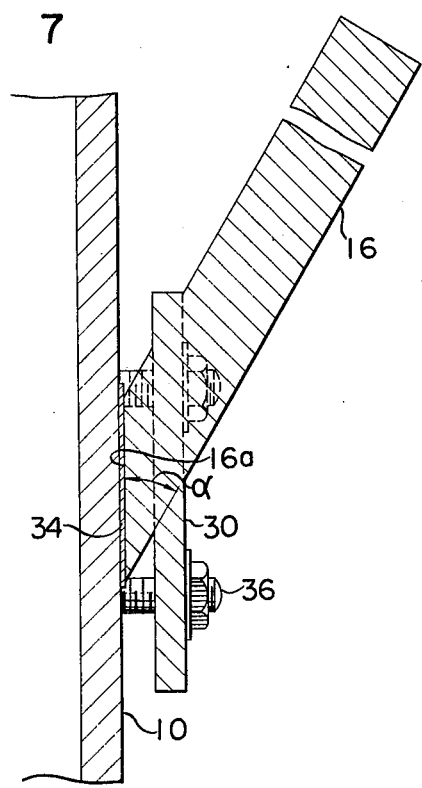
FIGS. 7 and 8 are view similar to FIG. 6 but illustrating different modifications of the arrangement shown in FIGS. 5 and 6.

In FIG. 7 wherein like reference numerals designate components identical or similar to those shown in FIGS. 5 and 6, there is illustrated a modification of the arrangement as shown in FIGS. 5 and 6. In FIG. 7, the mounting seat 32 as shown in FIG. 6 is omitted and the bolts 36 are directly provided in the outer wall of the pipe 10. In other respects the arrangement is substantially identical to that shown in FIGS. 5 and 6.

Figure 8:
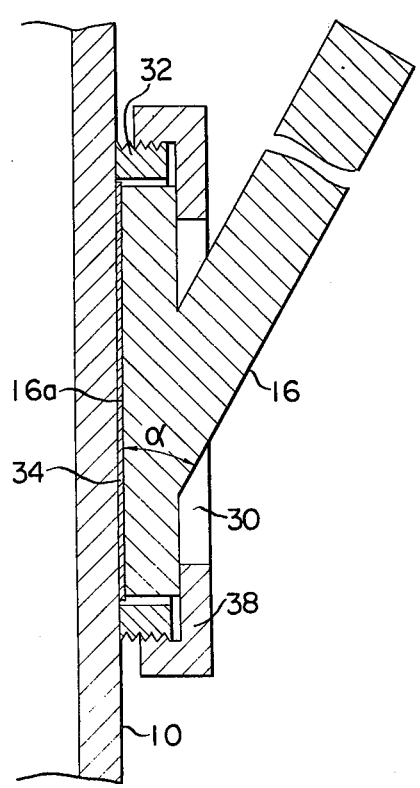

Another modification of the arrangement as shown in FIGS. 5 and 6 is illustrated in FIGS. 8 wherein like reference numerals designate the components identical or similar to those illustrated in FIGS. 5 and 6. As shown in FIG. 8, the guide rod 16 has fixedly secured to one end thereof a disc-shaped flange 30 including the abutting surface 16a as above described. The flange 30 is positioned within a circular opening on the mounting seat 32 fixed to the predetermined portion of the outer wall of the pipe 10. Then an apertured cap 38 through which the guide rod 16 is loosely extended engages threads disposed on the outer peripheral wall surface of the mounting seat 32 whereby the flange 30 is pressed and fixed against and to the outer wall surface of the pipe 10.

In summary, the present invention provides an ultrasonic flow meter device comprising a first ultrasonic transmitter and a receiver disposed on an outer wall surface of a pipe having flowing therethrough a fluid the velocity of which is to be measured and including a propagation path for an ultrasonic wave running within the fluid in the direction of flow thereof to produce a first sing-around frequency, a second ultrasonic transmitter and a receiver disposed on the outer wall surface of the pipe and including a propagation path for an ultrasonic wave running within the fluid in a direction opposite to the direction of flow of the fluid to produce a second sing-around frequency, and detector means for detecting the difference between the first and second sing-around frequencies to provide a measure of the flow rate of the fluid. Each of the transmitters and receivers is fixedly secured to a predetermined portion of the outer wall surface of the pipe through a guide rod having on the outer peripheral surface a plurality of ridges in a predetermined pattern so that ultrasonic waves reflected from the ridged surface of the guide rod cancel one another out. This ensures that the transmitters and receivers are maintained at permissible temperatures even when the fluid has high temperature.

In addition, each of the guide rods is fixed to the predetermined portion of the outer wall surface of the pipe through a thin sheet of gold or platinum or an alloy thereof. Therefore the present device can be operated with a fluid having a high temperature without the deterioration of the transmissibility of the ultrasonic waves at the interface between the guide rod and the pipe. This produces the result that the flow rate of a fluid at a high temperature can be measured without contacting the fluid.

While the present invention has been illustrated and described in conjunction with a few preferred embodiments thereof it is to be understood that numerous changes and modifications may be resorted to without departing from the spirit and scope of the present invention.

What we claim is:

1. An ultrasonic flow meter device comprising a pipe through which a fluid the velocity of which is to be measured flows, first ultrasonic transmitter and receiver means disposed on the outer wall surface of said pipe and including a propagation path for an ultrasonic wave running within said fluid in the direction of flow thereof to produce a first sing-around frequency, second ultrasonic transmitter and receiver means disposed on the outer wall surface of said pipe and including a propagation path for an ultrasonic wave running within said fluid in a direction opposite to the direction of flow of the fluid to produce a second sing-around frequency, detector means coupled to said first and second transmitter and receiver means for detecting a difference between said first and second sing-around frequencies to measure a flow rate of the fluid, each of said first and second ultrasonic transmitter and receiver means having an ultrasonic transmitter element and an ultrasonic receiver element, a guide rod for each of said elements on one end of which the corresponding element is mounted, each guide rod having on the outer peripheral surface thereof a plurality of ridges for causing ultrasonic waves reflected from the ridged surface of said guide rod to cancel one another out, means securing the other end of each said guide rod to the outer wall surface of pipe, and a thin sheet of a metallic material selected from the group consisting of gold, platinum, gold alloys and platinum alloys between said other end of each guide rod and the outer wall surface of said pipe.

2. An ultrasonic flow meter device comprising, in combination, a pipe through which a fluid the velocity of which is to be measured flows, a first ultrasonic transmitter element for producing a first ultrasonic wave traveling within said fluid through said pipe and in the direction of flow of the fluid, a first ultrasonic receiver element for receiving said first ultrasonic wave from said first ultrasonic transmitter element through said pipe, a second ultrasonic transmitter element for producing a second ultrasonic wave traveling within said fluid through said pipe and in a direction opposite to the direction of flow of the fluid, a second ultrasonic receiver element for receiving said second ultrasonic wave from said second ultrasonic transmitter element through said pipe, one guide rod connected between each of said elements and the adjacent portion of the outer wall surface of said pipe, said guide rod having on the outer peripheral surface a plurality ridges for causing ultrasonic waves reflected from the ridged surface of said guide rods to cancel one another out, a thin sheet between each of said guide rods and the adjacent portion of the outer wall surface of said pipe, said thin sheet being of a metallic material selected from the group consisting of gold, platinum, gold alloys and platinum alloys, and detector means coupled to said elements for detecting a difference in frequency between said first and second ultrasonic waves received by said first and second ultrasonic receiver elements respectively to determine the flow rate of the fluid.

3. An ultrasonic flow meter device as claimed in claim 2 wherein said guide rods each have a flange member engaging the end thereof at said pipe, and bolt means extending through said flange member for fixedly securing the end of said guide rod to said pipe with said thin sheet held tightly between said guide rod and said pipe.

4. An ultrasonic flow meter device as claimed in claim 2 wherein said guide rods each have a flange member on one end thereof, and an annular threaded cap over said flange and an annular threaded mounting seat on said pipe threadedly engage by said cap for to fixedly securing said guide rod to said pipe with said thin sheet held tightly between said flange and said pipe.

* * * * *